United States Patent [19]

Krzeminski

[11] 4,428,371

[45] Jan. 31, 1984

[54] INTRAUTERINE CONTRACEPTIVE LOADING DEVICE AND METHOD

[75] Inventor: Melvin L. Krzeminski, Palatine, Ill.

[73] Assignee: G. D. Searle & Co., Skokie, Ill.

[21] Appl. No.: 321,995

[22] Filed: Nov. 16, 1981

[51] Int. Cl.³ ............................................. A61F 5/46
[52] U.S. Cl. .................................. 128/130; 128/127
[58] Field of Search .............................. 128/127–131; 604/55, 1–2

[56] References Cited

U.S. PATENT DOCUMENTS

| | | | |
|---|---|---|---|
| 1,008,815 | 11/1911 | Grube | 604/1 |
| 2,034,416 | 3/1936 | Peat | 604/1 |
| 2,090,354 | 8/1937 | Massman | 604/2 |
| 3,674,007 | 7/1972 | Freis | 604/1 |
| 3,777,748 | 12/1973 | Abramson | 128/130 |
| 4,249,525 | 2/1981 | Krzeminski | 128/130 |

*Primary Examiner*—Henry J. Recla
*Assistant Examiner*—Karin M. Reichle
*Attorney, Agent, or Firm*—Mark I. Feldman

[57] ABSTRACT

A method and apparatus are provided for loading an intrauterine contraceptive device into the barrel of an inserter. The device includes an apertured tubular section having a closed end section at one end. The closed end defines an enlarged chamber. The device has a stem, a flexible arm generally transverse to the stem, and an enlarged head at one end of the stem. The device is receivable in the instrument when the stem is partially disposed within the barrel and the barrel is displaced forwardly until the head is received in the chamber. The head engages the shoulder that is defined between the aperture and the chamber in the instrument, thereby to retain the device in the instrument when the barrel is withdrawn. The device is removable from the instrument when the barrel is inserted again into the instrument to dislodge the head from the shoulder so that the barrel can be withdrawn together with the device.

8 Claims, 9 Drawing Figures

INTRAUTERINE CONTRACEPTIVE LOADING DEVICE AND METHOD

BACKGROUND OF THE INVENTION

1. Field of the Invention

This invention relates to intrauterine contraceptive devices and more particularly to a method and apparatus for loading the device onto the barrel of an inserter.

2. Description of the Prior Art

It has long been recognized that the presence of a foreign object in the uterus tends to prevent conception. In general, however, such devices must occupy a significant portion of the space in the uterus, and because the effective dimension of these devices is often larger than that of the nulliparous cervical canal, a dilation procedure requiring general anesthesia is often required to satisfactorily insert the devices.

In commonly assigned U.S. Pat. No. 3,777,748, the contents of which are incorporated herein by reference, an intrauterine contraceptive device is disclosed which could be conveniently emplaced without resorting to dilation of the nulliparous cervical canal. This device is known and referred to hereinafter as the "Cu-7" and it is generally in the shape of the numeral "7." It is comprised of a generally longitudinal arcuate stem member and an arcuate arm member which extends transversely from the terminal end of the stem member. The transverse arm of the Cu-7 is flexible so that it can be folded in overlying relationship with the longitudinal stem.

Conventionally, the Cu-7 device is emplaced in the uterine cavity by means of an inserter which consists of an elongated tube or barrel that is adapted to extend through the cervical opening and into the uterine cavity. The Cu-7 device is emplaced and loaded in the inserter by folding the transverse arm against the longitudinal stem, after which the end of the inserter barrel holding the Cu-7 is inserted into the uterine cavity via the vaginal and cervical openings. After the device is inserted at an appropriate depth in the uterine cavity, the device is expelled from the inserter by means of pressure exerted on its posterior portion by a forward moving piston that is disposed inside the inserter barrel. As the lateral pressure exerted on the transverse arm by the tubular inserter is released, that resilient arm springs apart from the longitudinal arm and bears firmly against the uterine wall at its terminal end while a large portion of the longitudinal arm also makes contact with the uterine walls such that the device is firmly lodged in the uterine.

It is found, however, that if the transverse end of the Cu-7 device is folded against the longitudinal arm for an extended period of time it may tend to lose some of its elasticity. It may therefore fail to regain its original "7" shape when expelled from the inserter. For this reason, it is undesirable to pre-position the Cu-7 device in its folded insertion position for an extended period of time.

Another disadvantage of the conventional devices is that the process of manually inserting the device into the canal is difficult and time consuming especially since it must be done with examination gloves so as to maintain the sterility of the device.

SUMMARY OF THE INVENTION

The foregoing disadvantages of the prior art are overcome in accordance with the present invention which provides an intrauterine contraceptive loading device and a method for loading the device onto the barrel of an inserter. The intrauterine contraceptive device has a longitudinal stem section and a flexible arm that depends from one end of the stem section. The device also includes an enlarged head section at the one end of the stem section.

The loading instrument comprises an elongated column which has a longitudinal axis. The column comprises a tubular section that defines an axially extending through aperture, and a closed end section at one end of the column. The aperture is dimensionally adapted to receive the device. The closed end section of the column defines a chamber that communicates with the opening. The chamber has a greater cross-sectional dimension than the aperture. The distal end of the tubular section defines a shoulder that surrounds the opening.

The closed end section has a rear wall that comprises stop means to limit insertion of the device and barrel into the instrument.

The intrauterine contraceptive device is receivable in the instrument when the device is mounted inside the barrel of the inserter and then displaced forwardly until the head is received in the chamber. The head is engageable with the shoulder to retain the device in the instrument when the barrel is withdrawn. The device is removable from the instrument when the barrel is inserted again into the instrument to move the head out of engagement with the shoulder so that the barrel can be withdrawn together with the device.

A method of loading an intrauterine contraceptive device onto the barrel of an inserter comprises the steps of providing a loading instrument that defines an aperture which terminates in an enlarged chamber, the instrument defining a shoulder between the aperture and the chamber; initially positioning the intrauterine contraception device with the arm having a free end spaced from the stem section, with a portion of the stem section positioned within the barrel and the entire flexible arm positioned outside the barrel; inserting the barrel with the mounted device into the aperture until the head is positioned in the chamber, thereby displacing the arm into overlying relationship with the stem, with the stem positioned within the barrel and the arm positioned outside the barrel; engaging the head with the shoulder; withdrawing the barrel from the device until the barrel is withdrawn past the end of the arm; moving the barrel back into the aperture with the flexible arm and the stem both being received in the barrel, the barrel being moved until the barrel is proximate the head; releasing the head from the shoulder; and withdrawing the inserter from the instrument, whereby the device is carried by the instrument with the arm and stem positioned within the barrel.

The present invention enables the intrauterine contraceptive device to be stored with the flexible arm spaced from the stem, and provides for quickly and easily loading the device so that both the flexible arm and the stem are positioned within the barrel of the inserter. Moreover, by providing the instrument within a sterilized bag, the device can be loaded into the barrel under sterile conditions without touching the device.

DETAILED DESCRIPTION OF THE PREFERRED EMBODIMENT

Figure 1:
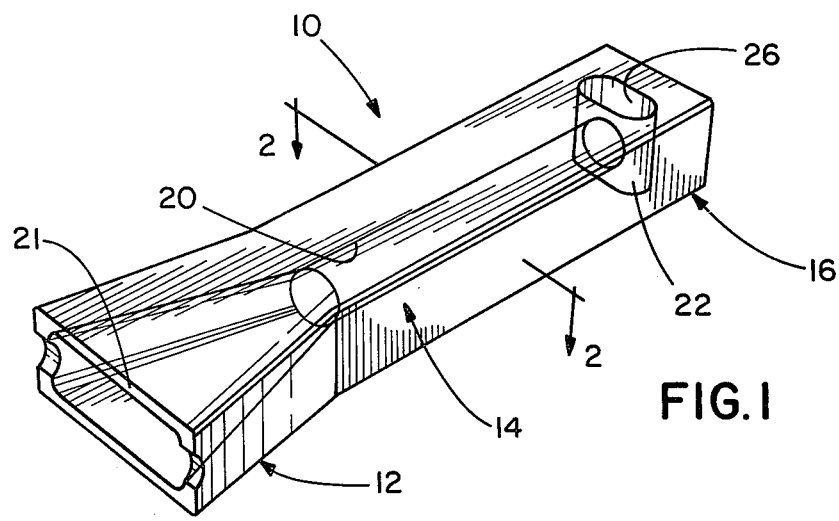
FIG. 1 is a perspective view of the loading instrument of the present invention.
Figure 2:
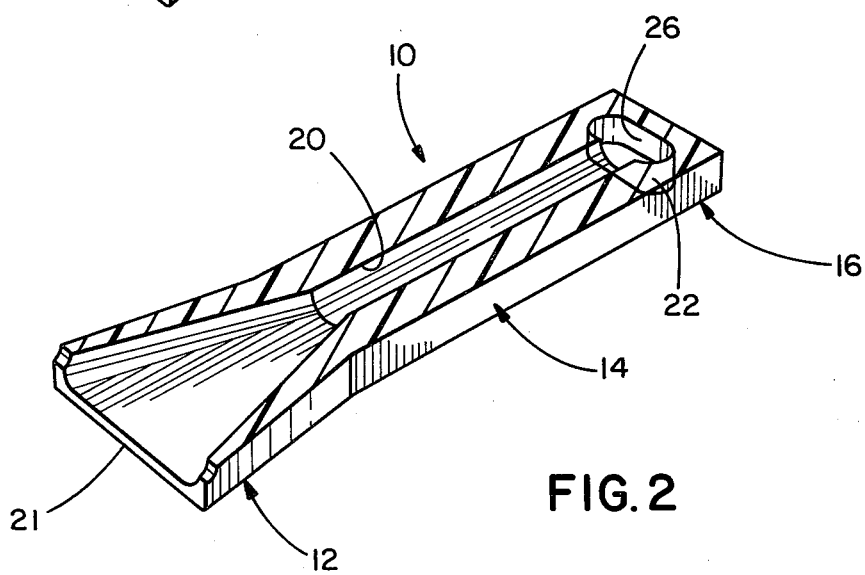
FIG. 2 is a cross-sectional view taking along line 2—2 of FIG. 1.

While this invention is susceptible of embodiment in many different forms, there is shown in the drawings and will herein be described in detail one specific embodiment, with the understanding that the present disclosure is to be considered as an exemplification of the principles of the present invention, and is not intended to limit the invention to the embodiment illustrated.

Referring now to the drawings, FIG. 1 shows the loading instrument 10 of the present invention which comprises an elongated column having a longitudinal axis. The column includes a funnel section 12 at one end, an intermediate tubular section 14, and a closed end section 16. The funnel section 12 and tubular section 14 each define an aperture 20 which extends along the axis of the column.

The funnel section extends from the front end 21 of the instrument to the intermediate section 14. The cross-sectional dimension of the aperture 20 is greatest at the front end 21, and gradually tapers to a smaller cross-sectional dimension at the junction with the intermediate section 14. In the illustrated embodiment, the size of the aperture 20 is uniform along the length of the intermediate section 14.

The closed end section 16 of the column defines a chamber 22 that communicates with the aperture 20, and may comprise a through opening that is normal to the axis of the aperture 20. The chamber 22 has a greater cross-sectional dimension than the aperture. The distal end of the tubular section 14 defines a shoulder 24 (FIG. 3) that surrounds the aperture.

The closed end 16 has a rear wall 26 that comprises stop means. Thus, the column comprises a generally tubular member that has an open end and a closed end that is defined by the rear wall 26.

Figure 3:
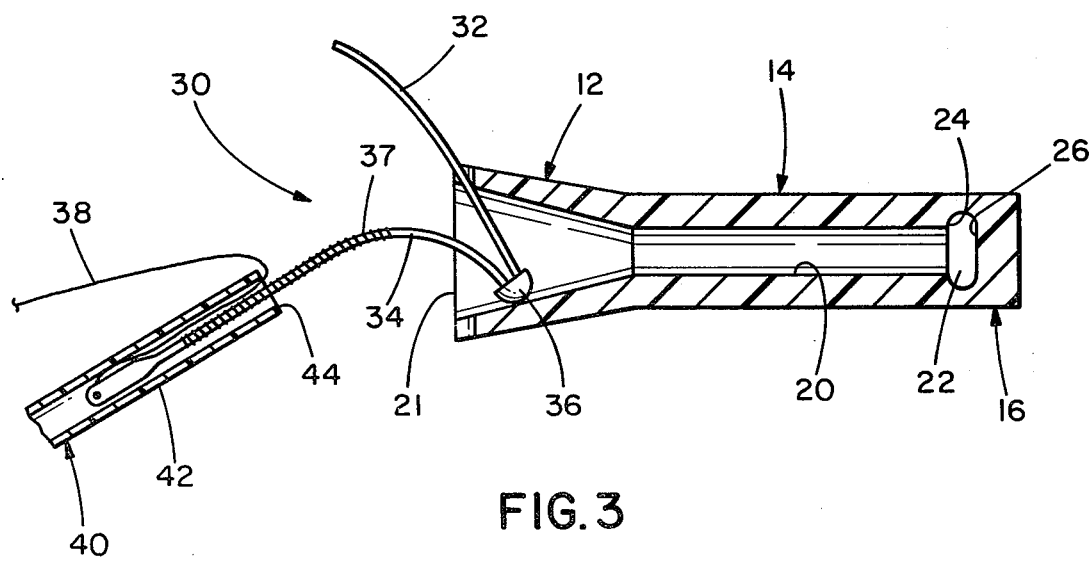
FIGS. 3 through 9 are cross-sectional views of the loading instrument of the present invention, showing the intrauterine contraception device and the barrel of the inserter in various stages of loading, with the barrel being shown in fragment.

The intrauterine contraceptive device 30 that is used with the loading instrument 10 preferably is generally in the shape of the numeral "7", as shown in FIG. 3 and comprises transverse arm 32 and longitudinal stem 34 dependent therefrom substantially at one end thereof. Both the transverse arm 32 and longitudinal stem 34 are flexible, and have a memory for the rest position shown in FIG. 3. However, a major portion of the longitudinal stem spaced from the head 36 is wound with a copper wire 37, and the copper wire reduces the flexibility of the longitudinal stem 34. The intrauterine contraceptive device is disclosed more fully in commonly assigned U.S. Pat. No. 3,777,748, the contents of which are incorporated herein by reference.

As shown in FIG. 3, the flexible arm 32 and the longitudinal stem 34 are joined at an enlarged head section 36, which comprises a substantially hemispherical nub or mushroom-shaped tip. This provides a generally rounded surface which facilitates insertion of the device into the cervical canal and minimizes any irritation that might occur.

The device includes a filament 38 which is attached to the terminal portion of the device to facilitate removal from the uterus and, in some cases, to aid insertion into the uterine cavity.

Referring again to FIG. 3, the loading instrument 10 is adapted for use with an inserter 40 which includes a tubular barrel 42. The inserter is described in the aforementioned U.S. Pat. No. 3,777,748. The barrel 42 has an inside diameter that is large enough to receive the flexible arm 32 and longitudinal stem 34. The inside diameter of the barrel 42 preferably is smaller than the outside diameter of the head 36, so that the head will not fit within the barrel. As a result, the distal end 44 of the barrel forms a stop means to limit the insertion of the device 30 within the barrel.

Figure 4:
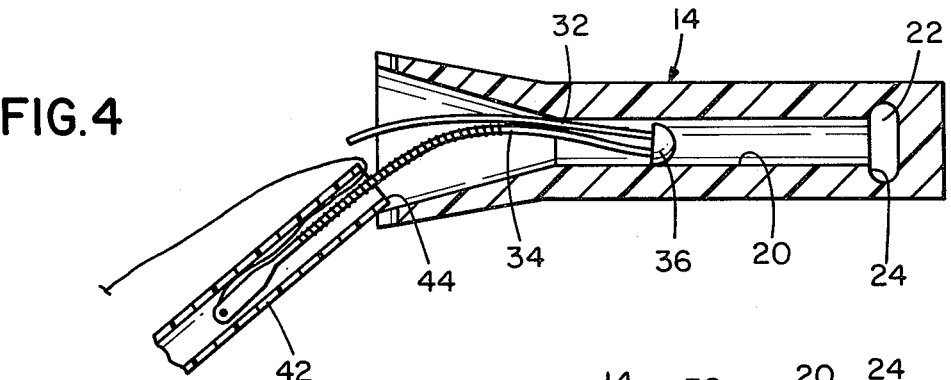

As shown in FIG. 4, the aperture 20 is dimensionally adapted to receive the device 30. Accordingly, the inside diameter of the aperture 20 is greater than the outside diameter of the enlarged head 36 of the contraceptive device 30. The aperture 20 is also adapted to receive the barrel 42, and has an inside diameter that is greater than the outside diameter of the barrel.

The sequence of steps for using the loading instrument is described with reference to FIGS. 3 through 9. Referring initially to FIG. 3, the device 30 in the rest condition has the flexible arm 32 generally transverse to longitudinal stem 34. The flexible arm 32 has a free end that is spaced from the longitudinal stem 34. A portion of the stem 34 is positioned within the barrel 42, and the entire flexible arm 32 is positioned outside the barrel. The device 30 and inserter 40 can be prepackaged in this position.

As shown in FIG. 3, the head 36 is inserted into the aperture in the funnel section 12 of the loading instrument. The barrel 42, which partially receives the stem 34, is positioned at an angle relative to the loading instrument 10, as depicted in FIG. 3, to facilitate insertion of the head into the funnel 12. The inside wall of the instrument which defines the aperture in the funnel section 12 is at an angle relative to the axis of the aperture to further facilitate the receipt and guidance of the device in the funnel; the angle preferably is about 30 degrees.

Referring to FIGS. 3 and 4, the barrel 42 is moved to the right to insert the barrel with the mounted device into the aperture 20. The barrel is maintained at an angle relative to the axis of the instrument. The funnel section 12 of the loading instrument guides the device 30 into the tubular section 14 of the loading instrument, while simultaneously compressing the flexible arm 32 of the device against the outside of the barrel 42.

Figure 5:
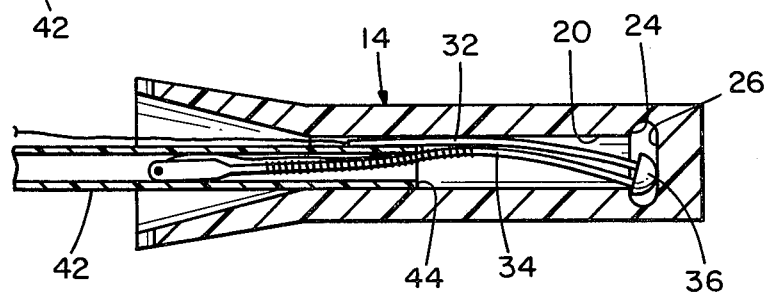

The barrel is inserted into the aperture 20 until the head 36 is positioned in the chamber 22, as illustrated in FIG. 5. As the barrel is pushed into the instrument from the position of FIG. 4 to the one shown in FIG. 5, the user rotates the barrel until it is coaxial with the aperture 20. In the position depicted in FIG. 5, a portion of the longitudinal stem 34 is received within the barrel 42, and a portion of the flexible arm 32 overlies the outside surface of the barrel. When the head 36 is received in the chamber, the inherent resiliency and flex of the stem 32 and arm 34 causes the head to be displaced transversely, thereby engaging the bottom surface of the head with the shoulder 24. In order to accommodate the head 36, the chamber 22 has a length along the axis of the instrument that is greater than the height of the head. The rear wall 26 functions as a stop means to limit the insertion of the device 30 into the instrument.

Figure 6:
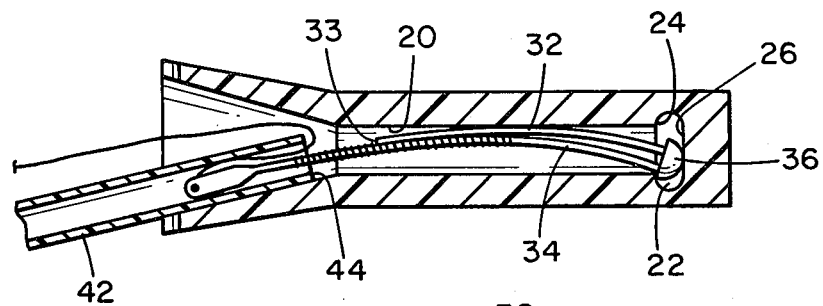

As shown in FIG. 6, the barrel 42 is then withdrawn from the device until the distal end 44 of the barrel is withdrawn past the distal end 33 of the transverse arm. The device 30 remains fixed in the instrument 10 while the barrel is withdrawn because of the engagement of the head 36 against the shoulder 24. In the position shown in FIG. 6, the transverse arm 32 overlies the longitudinal stem 34, with the end of the transverse arm being in engagement with the longitudinal stem due to the inherent resiliency of the arm and stem.

Figure 7:
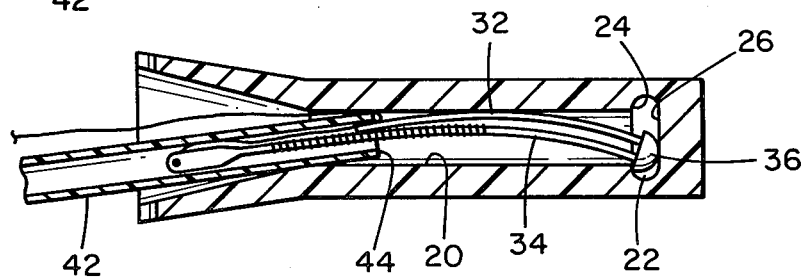
Figure 8:
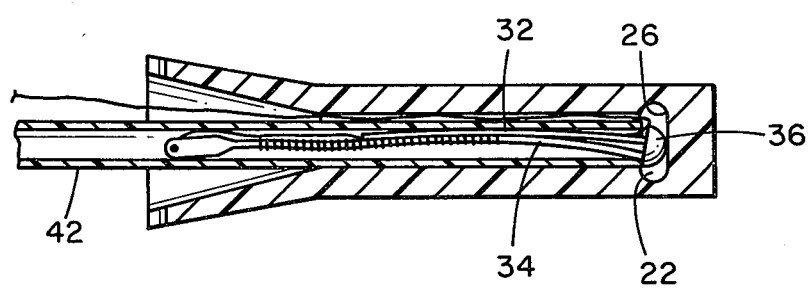

The barrel is then moved back into the aperture 20, as shown in FIG. 7, with the transverse arm 32 and the longitudinal stem 34 both being received within the barrel 42. The barrel is moved inwardly, to the right, into the loading instrument until the distal end 44 of the barrel engages the head 36, as shown in FIG. 8. The movement of the barrel 42 along the instrument until it engages the head causes the head to become displaced transversely until it is approximately coaxial with the aperture 20, thereby dislodging and releasing the head 36 from the shoulder 24. The resiliency of the transverse arm and longitudinal stem cause portions thereof to frictionally engage the inside wall of the barrel 42, as depicted in FIG. 8.

Figure 9:
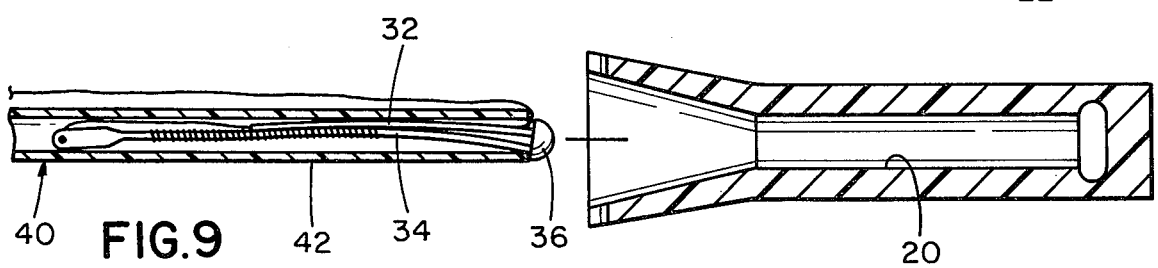

The barrel 42 is then withdrawn from the loading instrument 10, by moving the barrel to the left, as shown in FIG. 9. Because of the frictional engagement between the device 30 and the barrel 42, the device is carried by the barrel, with the transverse arm 32 and longitudinal stem positioned within the barrel, and the head 36 is proximate the distal end 44 of the barrel. The device 30 is then available for insertion and placement within the uterine cavity in a conventional manner by means of the inserter.

By way of example, and not as a limitation, the distance from the junction of the funnel section and the intermediate section, to the front of the rear wall 26, preferably is about equal to 1.050 inches, which is the transverse arm length (about 1.014 inches) plus approximately one millimeter tolerance. The inside diameter of the aperture 20 along the intermediate section 14 preferably is about 0.156 inch, which equals the outside diameter of the barrel (about 0.120 inches) plus about one millimeter tolerance. The width of the chamber 22 preferably is about 0.106 inch, which equals the length of the head 36 (about 0.070 inch) plus about one millimeter tolerance.

The device may be prepackaged in a sealed pouch (not shown) with the device partially received in the barrel, as shown in FIG. 3. The instrument is also provided in the package and preferably is fixedly positioned, as by being mounted to a support card. To load the device with both the arm and stem in the barrel, one end of the package is opened, and the inserter is held and manipulated relative to the instrument as described hereinabove, all while the device and instrument remain within the pouch and without directly touching either the device or pouch, so that the device is loaded aseptically.

From the foregoing, it will be observed that numerous variations and modifications may be affected without departing from the true spirit and scope of the novel concept of the invention. It is to be understood that no limitation with respect to the specified device illustrated herein and the method described herein is intended or should be inferred. It is, of course, intended to cover by the appended claims all such modifications as fall within the scope of the claims.

What is claimed is:

1. An intrauterine contraceptive loading apparatus, comprising:
    an intrauterine contraceptive device having a longitudinal stem section and a flexible arm depending from one end of the stem section, and an enlarged head at said one end of the stem section,
    a generally tubular inserter barrel, and
    a loading instrument comprising an elongated column having first and second ends and a longitudinal axis, said column comprising a tubular section that defines an aperture extending axially therethrough from said first end, said column having a closed end section at the second end thereof, said aperture being dimensionally adapted to receive said intrauterine contraceptive device and said inserter barrel,
    said closed end section of said column having a chamber therein that communicates with said aperture, said chamber having a greater cross-sectional dimension than said aperture, the interface of said tubular section and said aperture defining a shoulder surrounding said aperture, said head of said intrauterine contraceptive device being movable between a position in engagement with said shoulder and another position without engaging said shoulder,
    said closed end section having a rear wall that comprises stop means to limit insertion of said intrauterine contraceptive device and barrel into said instrument, whereby the longitudinal stem section of the intrauterine device is partially received inside the barrel of the inserter with the flexible arm outside said barrel and then displaced into the tubular section of the loading instrument until the head is received in the chamber, said head being engageable with the shoulder to retain said device in said instrument, said barrel being withdrawn until the barrel is past the end of said arm, said barrel being displaced back into said tubular section with both said stem and said arm within said barrel until said barrel is proximate said head, said device being removable from the instrument by said barrel moving said head out of engagement with said shoulder so that said barrel can be withdrawn together with said device.

2. An apparatus as defined in claim 1 wherein said tubular section comprises a converging section extending from said first end of said column and an intermediate section between said converging section and said chamber, said aperture extending through said converging section and said intermediate section, said aperture in said intermediate section communicating said converging section with said chamber.

3. An apparatus as defined in claim 1 wherein said aperture in said converging section has a predetermined diameter adjacent said intermediate section, and an enlarged cross-sectional dimension adjacent the first end of said column, said aperture being tapered between said first end and said intermediate section to define guide means for receiving said intrauterine contraceptive device in said instrument.

4. A method of loading an intrauterine contraceptive device into an inserter having a barrel, said intrauterine contraceptive device having a longitudinal stem section and a flexible arm depending from one end of the stem section, and an enlarged head section at said one end of the stem section, comprising the steps of:
    providing a loading instrument having a first end and a second end, said loading instrument including an enlarged chamber adjacent said first end and an aperture that extends through the second end to said chamber, said aperture having a longitudinal axis, said instrument defining a shoulder between said aperture and said chamber, initially positioning said intrauterine contraceptive device with said arm having a free end spaced from said stem section, with a portion of said stem section positioned within said barrel and the entire flexible arm positioned outside said barrel, inserting said barrel with said intrauterine contraceptive device into said aperture until said head is positioned in said chamber, thereby displacing said arm into overlying relationship with said stem, with said stem positioned within said barrel and said arm positioned outside said barrel, engaging said head with said shoulder, withdrawing said barrel from said intrauterine contraceptive device until said barrel is withdrawn past the end of said arm, moving said barrel back into said aperture with said flexible arm and said stem both being received in said barrel, said barrel being moved until said barrel is proximate said head, releasing said head from said shoulder with said inserter, and withdrawing said barrel from said instrument, whereby said intrauterine contraceptive device is carried by said barrel with said arm and stem positioned within said barrel.

5. A method as defined in claim 4 including the step of moving said head transversely into non-axial alignment with said aperture to engage said head with said shoulder.

6. A method as defined in claim 4 including the step of moving said head into axial alignment with said aperture to release said head from said shoulder.

7. A method of loading an intrauterine contraceptive device into an inserter having a barrel, said intrauterine contraceptive device having a longitudinal stem section and a flexible arm depending from one end of the stem section, and an enlarged head section at said one end of the stem section, comprising the steps of:

providing a loading instrument having a first end and a second end, said loading instrument including an enlarged chamber adjacent said first end and an aperture that extends through the second end to said chamber, said aperture having a longitudinal axis, said instrument defining a shoulder between said aperture and said chamber, initially positioning said intrauterine contraceptive device with said arm having a free end spaced from said stem section, displacing said inserter barrel toward said intrauterine contraceptive device to mount said stem in said barrel, inserting said barrel with said intrauterine contraceptive device into said aperture until said head is positioned in said chamber, displacing said arm into overlying relationship with said stem, with said stem positioned within said barrel and said arm positioned outside said barrel, engaging said head with said shoulder, withdrawing said barrel from said device until said barrel is withdrawn past the end of the said arm, moving said barrel back into said aperture with said flexible arm and said stem both being received in said barrel, said barrel being moved until said barrel is proximate said head, releasing said head from said shoulder with said inserter, and withdrawing said barrel from said instrument, whereby said intrauterine contraceptive device is carried by said barrel with said arm and stem positioned within said barrel.

8. A method as defined in claim 7 including the steps of moving said head transversely into non-axial alignment with said aperture to engage the head with the shoulder, and moving the head into axial alignment with said aperture to release the head from the shoulder.

* * * * *